United States Patent [19]

Straw et al.

[11] Patent Number: 4,985,021
[45] Date of Patent: Jan. 15, 1991

[54] SAFETY ENCLOSURE SYSTEM FOR MEDICAL DEVICES

[75] Inventors: Jeff Straw, 1347 Ramona Dr., Racine, Wis. 53406; C. Thomas Sylke, Milwaukee, Wis.

[73] Assignee: Jeff Straw, Racine, Wis.

[21] Appl. No.: 304,256

[22] Filed: Jan. 31, 1989

[51] Int. Cl.⁵ .............................................. A61M 5/32
[52] U.S. Cl. .................................... 604/198; 604/263
[58] Field of Search ............... 604/198, 187, 263, 110, 604/195

[56] References Cited

U.S. PATENT DOCUMENTS

| | | | |
|---|---|---|---|
| 4,631,057 | 12/1986 | Mitchell | 604/198 |
| 4,681,567 | 7/1987 | Masters et al. | 604/198 |
| 4,795,432 | 1/1989 | Karczmer | 604/198 X |
| 4,820,275 | 4/1989 | Haber et al. | 604/198 |
| 4,850,977 | 7/1989 | Bayless | 604/198 |
| 4,850,994 | 7/1989 | Zerbst et al. | 604/198 |

FOREIGN PATENT DOCUMENTS 598257 9/1959 Italy .................................... 604/198

Primary Examiner—John D. Yasko
Attorney, Agent, or Firm—C. Thomas Sylke; Arnold J. Ericsen

[57] ABSTRACT

A system for protecting an individual against injury or infection from a sharp instrument such as a needle or syringe includes a sheath slidably attached to the mounting. The sheath is locked in an open position during use of the needle and syringe. After use, the sheath is rotated to unlock the protective mechanism. A spring urges the sheath over the needle, thereby enclosing the needle and protecting anyone handling the instrument from injury. The sheath is maintained in its enclosing position by a locking flange in the interior of the sheath which engages an abutting ring on the mounting.

1 Claim, 1 Drawing Sheet

SAFETY ENCLOSURE SYSTEM FOR MEDICAL DEVICES

BACKGROUND OF THE INVENTION

1. Field of the Invention

The present invention relates generally to medical and health equipment used in hospitals, clinics and other health related facilities. More particularly, the present invention relates to a mechanism designed to protect individuals from injury or infection from contaminated needles or other sharp objects used in the diagnosis and treatment of health conditions.

2. Description of the Prior Art

Various designs for disposable syringes abound. U.S. Pat. No. 4,469,482 issued Sept. 4, 1984 to Lissenburg, et al for a "Disposable Hypodermic Syringe" shows one such disposable syringe construction. Similarly, designs have been created to prevent tampering with a syringe prior to use. For example, U.S. Pat. No. 4,571,242 issued Feb. 18, 1986 to Klein for a "Tamper Proof Cap For Syringes And The Like" shows a tamper-proof sealing cap for a syringe.

There are also designs which provide certain safety features during use of the syringe. Examples of such designs are found in U.S. Pat. No. 4,391,272 issued on July 5, 1983 to Staempfli for a "Disposable Syringe" and U.S. Pat. No. 4,185,691 issued on Jan. 29, 1980 to Reiss for "Retractable Shield For Syringes". Staempfli shows a syringe construction which prevents reversal of the plunger mechanism direction when the plunger is being used to inject a fluid. Reiss discloses a multiple shield device designed to protect a user against exposure from radioactive materials.

In U.S. Pat. No. 4,391,273 issued on July 5, 1983 to Chiquiar-Arias for "Non-Reusable, Disposable Syringes", a self-destructing element is incorporated into the syringe design so that as the syringe is being used, it is likewise being impaired for future use. However, the user is not protected from the contaminated needle. Likewise, the design is particular to syringes and is not apparently adaptable to other piercing or cutting devices used in the health care field.

U.S. Pat. No. 4,270,536 issued June 2, 1981 to Lemelson for a "Disposable Syringe" shows a disposable hypodermic syringe which has a cavity in the piston in which the needle may be inserted and broken off after use. While this design is intended to prevent injury or infection from a contaminated needle, it nevertheless may provide sharp or jagged edges after breakage which may still cause injury or infection.

A design which would more effectively and economically accomplish the objects of designs such as Lemelson would prove to be a significant advancement in the art.

OBJECTS AND SUMMARY OF THE INVENTION

It is a primary object of the present invention to provide a simple protective mechanism to guard against infection or other injury to a person from a contaminated needle or other sharp object.

It is another object of the present invention to provide a protective mechanism which is easily and economically manufactured.

It is yet another object of the present invention to provide a protective mechanism which is adaptable to a variety of needles and other sharp objects currently used in the medical and health fields.

How these and other objects of the present invention are accomplished will be explained in a detailed description of the preferred embodiment of the present invention in connection with the FIGURES. Generally, however, the objects are accomplished in a system for protecting an individual against injury or infection from a sharp instrument such as a needle or syringe which includes a sheath slidably attached to the mounting. The sheath is locked in an open position during use of the needle and syringe. After use, the sheath is rotated to unlock the protective mechanism. A spring urges the sheath over the needle, thereby enclosing the needle and protecting anyone handling the instrument from injury. The sheath is maintained in its enclosing position by a locking flange in the interior of the sheath which engages an abutting ring on the mounting.

DESCRIPTION OF THE DRAWINGS

In the FIGURES, like reference numerals refer to like elements.

DESCRIPTION OF THE PREFERRED EMBODIMENT

Figure 1:
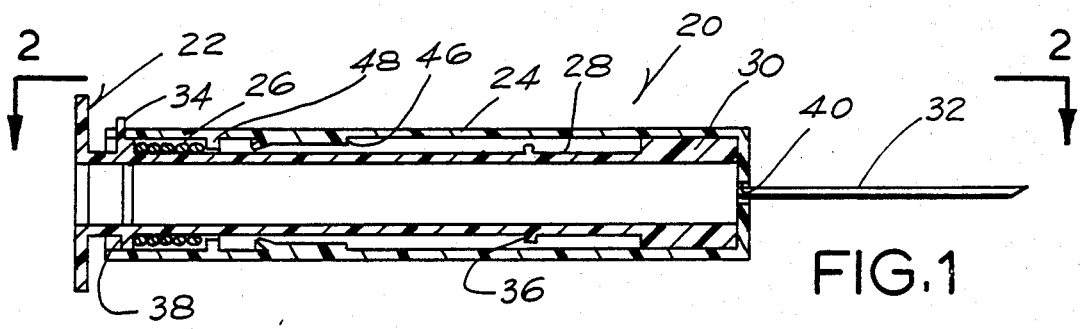
FIG. 1 is a cross-sectional view of the device of the present invention in its closed position.

The preferred embodiment of the present invention is shown in FIG. 1 and includes a syringe 22 utilizing a protective mechanism 20. The two basic elements used in the preferred embodiment of the protection mechanism are a sheath 24 and a spring 26.

Syringe 22 has a cylindrical tube 28 with a stopping flange 30 at one end adjacent needle 32. At the other end of syringe 22 is a locking post 34. Intermediate post 34 and flange 30 is a locking ring 36, the purpose of which will be explained in more detail below.

Sheath 24 has a hole 40 through which needle 32 extends during use of the syringe. Sheath 24, like syringe 22, is primarily composed of a cylindrical tube 42 having a generally open end opposite hole 40. Inside sheath 24 is a locking flange 44 which cooperates with locking ring 36 as described below. There is also a ledge 46 designed to cooperate with flange 30 in a way to be described below. Finally, sheath retaining ring 48 and syringe retaining ring 38 hold spring 26 in place and in a compressed state as shown in FIG. 1.

Operation

Figure 2:
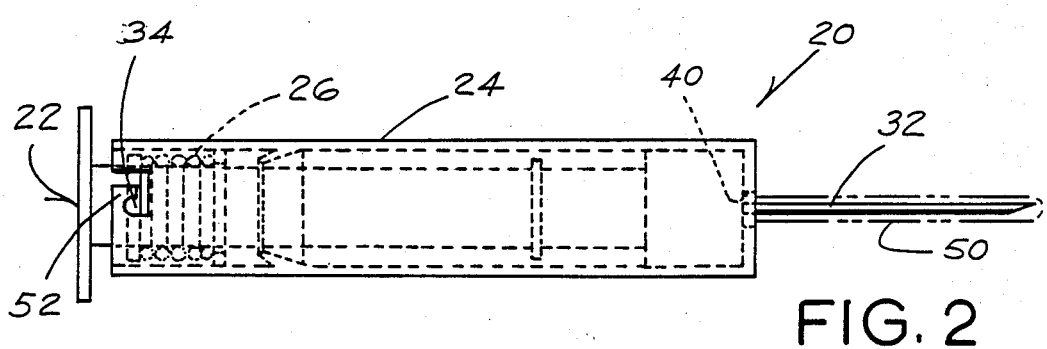
FIG. 2 is a top plan view of the device of the present invention taken along the line 2—2 of FIG. 1.

Initially, syringe 22 and sheath 24 are in the configuration shown in FIGS. 1 and 2. A protective cap 50 may be used over unused needle 32 to prevent injury of the user or contamination of the needle prior to use. Protective cap 50 is removed and the syringe is then used.

Once used, the syringe poses a potential health hazard both because the sharp needle 32 is exposed and could cause puncture wounds, as well as the possibility of infection from a used needle (including infection from the AIDS virus from patients who might be carrying that virus). Therefore, the protective mechanism 20 of the present invention may be used to enclose the needle 32 to protect any persons coming in contact with the used syringe.

Figure 3:
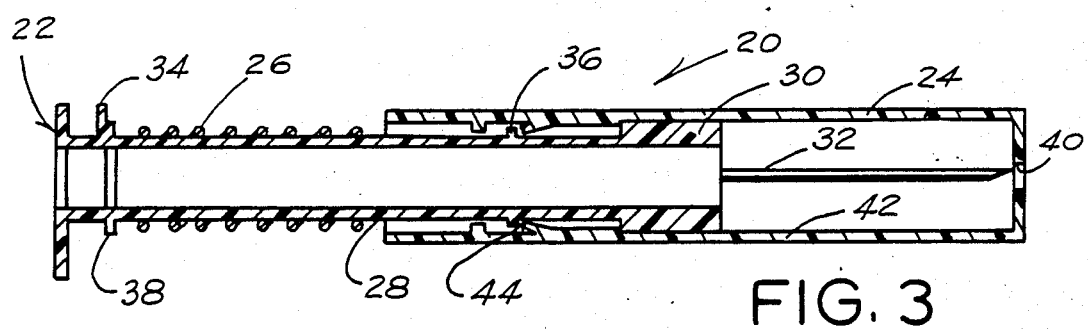
FIG. 3 is a cross-sectional view of the device of the present invention in its locked and open position.

To engage the protective mechanism, one rotates sheath 24 so that locking post 34 on syringe 22 is longitudinally clear of locking hook 52 on sheath 24. By releasing sheath 24, compressed spring 26 expands between retaining rings 38 and 48, propelling sheath 24 away from post 34. Upon reaching the appropriate point, locking flange 44 passes over locking ring 36, thereby securing sheath 24 in place. Sheath 24 is prevented from overextending by the engagement of flange 30 with ledge 46. This extended and locked position is shown in detail in FIG. 3.

After sheath 24 has been locked into place, it is safe for persons to handle the used syringe 22 without danger of injury or infection. The protective mechanism 20 may be made of a low cost plastic, so as to keep manufacture economical, as well as providing a flexible material which is necessary for locking flange 44 to be able to flexibly extend over locking ring 36.

As is apparent from the above description, this mechanism may be adapted to devices other than syringes. For example, in drawing blood samples, the needle used in that procedure (although not a syringe) may utilize a similar protective mechanism and locking feature so that once the blood sample has been drawn, the needle may be securably enclosed. Furthermore, devices such as scalpels, or other cutting or piercing articles, might be equipped with a similar protective mechanism to ensure safe handling and/or disposal after use.

Variations, modifications and other applications will become apparent to those skilled in the art. Therefore, the above description of the preferred embodiment is to be interpreted as illustrative rather than limiting. The scope of the present invention is limited only by the scope of the claims that follow.

What is claimed is:

1. An improved anticontamination mechanism for a syringe having a needle attached thereto, consisting of:
   a unitary and generally cylindrical tube having a needle attached at its first end to permit fluid to flow from said tube through said needle, said tube having an extended cylindrical shoulder at its first end, a locking ring intermediate said shoulder and the second end of said tube, a pin adjacent the second end of said tube, and an inner spring ring adjacent said pin;
   a unitary sheath slidable on said tube between a first retracted position and a second extended position, said sheath having a hook engageable with said pin when said sheath is in said first position, an outer spring ring, a flange unidirectionally engageable with said locking ring to lock said sheath in said second position, and a ledge located near the longitudinal center of said sheath and engageable with said shoulder when said sheath is in said second position;
   wherein said sheath is moved from said first position to said second position by a spring on said tube between said inner and outer spring rings when said hook is disengaged from said pin;
   further wherein said sheath is positively locked in said second position by first locking means comprising said flange engaging said locking ring to prevent movement of said sheath back toward said first position and second locking means comprising said ledge engaging said shoulder to positively prevent further movement of said sheath away from said first position and to prevent subsequent removal of said sheath from said tube; and
   further wherein approximately one half of said sheath concentrically engages said tube when said sheath is in said second position to further prevent subsequent removal of said sheath from said tube.

* * * * *